(12) United States Patent
Charles

(10) Patent No.: US 12,350,195 B2
(45) Date of Patent: Jul. 8, 2025

(54) METHODS AND APPARATUS FOR PERFORMING OCULAR BIOMETRY

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 621 days.

(21) Appl. No.: 17/407,226

(22) Filed: Aug. 20, 2021

(65) Prior Publication Data
US 2022/0062043 A1    Mar. 3, 2022

Related U.S. Application Data

(60) Provisional application No. 63/070,983, filed on Aug. 27, 2020.

(51) Int. Cl.
| | | |
|---|---|---|
| *A61F 9/007* | (2006.01) | |
| *A61B 3/10* | (2006.01) | |
| *A61B 3/103* | (2006.01) | |
| *A61B 3/107* | (2006.01) | |
| *A61F 2/16* | (2006.01) | |

(52) U.S. Cl.
CPC .......... *A61F 9/00736* (2013.01); *A61B 3/102* (2013.01); *A61B 3/103* (2013.01); *A61B 3/107* (2013.01); *A61F 2/16* (2013.01)

(58) Field of Classification Search
CPC .. A61B 3/13; A61B 3/14; A61B 3/102; A61B 3/0025; A61B 5/7207; A61B 3/1225; A61B 3/1173; A61B 3/103; A61B 3/107; A61B 3/1005; A61B 3/1015; A61B 34/10; A61F 9/00736; A61F 2/16; A61F 9/00827; A61F 9/00804; A61F 9/008; A61F 9/00829
See application file for complete search history.

(56) References Cited

U.S. PATENT DOCUMENTS

| | | | | |
|---|---|---|---|---|
| 11,826,244 B2 * | 11/2023 | Kojima | ................. | A61F 2/1694 |
| 2008/0004610 A1 * | 1/2008 | Miller | .................... | A61B 3/103 |
| | | | | 606/6 |

(Continued)

FOREIGN PATENT DOCUMENTS

WO    WO-2016115369 A1 *    7/2016    ........... B29C 64/129

OTHER PUBLICATIONS

Tranos Paris G. et al: "Comparison of postoperative refractive outcome in eyes undergoing combined phacovitrectomy vs cataract surgery following vitrectomy", Graefe's Archive for Clinical and Experimental Ophthalmology, Springer Verlag, DE, vol. 258, No. 5, Jan. 10, 2020, pp. 987-993, XP037095773, retrieved on Jan. 10, 2020, abstract, p. 988, 989, right hand-column, paragraph 2.

*Primary Examiner* — Rebecca E Eisenberg
*Assistant Examiner* — Rachel O'Connell

(57) ABSTRACT

Certain embodiments provide a method of performing ocular biometry. The method includes performing phacoemulsification to emulsify and remove an internal lens of an eye. The method further includes performing vitrectomy to remove vitreous from the eye. The method also includes placing a trial in a lens capsule of the eye. The method further includes performing biometry with a first biometry system to provide measurements including at least one of an axial length of the eye, a curvature of a cornea of the eye, and toric axis. The method also includes removing the trial from the lens capsule.

10 Claims, 8 Drawing Sheets

(56) References Cited

U.S. PATENT DOCUMENTS

| | | | |
|---|---|---|---|
| 2015/0088193 A1* | 3/2015 | Scheller | A61B 17/30 |
| | | | 606/207 |
| 2015/0230702 A1 | 8/2015 | Uhlhorn et al. | |
| 2016/0089026 A1* | 3/2016 | Heeren | G02B 27/0018 |
| | | | 351/207 |
| 2016/0150952 A1* | 6/2016 | Raymond | A61B 3/1015 |
| | | | 351/205 |
| 2018/0042768 A1* | 2/2018 | Charles | A61F 9/00727 |
| 2018/0296391 A1* | 10/2018 | Charles | A61M 1/7415 |
| 2019/0099262 A1* | 4/2019 | Ladas | G16H 50/50 |
| 2021/0244278 A1* | 8/2021 | Frisken | A61B 3/0008 |
| 2021/0369104 A1* | 12/2021 | Bleicher | G06T 7/70 |

\* cited by examiner

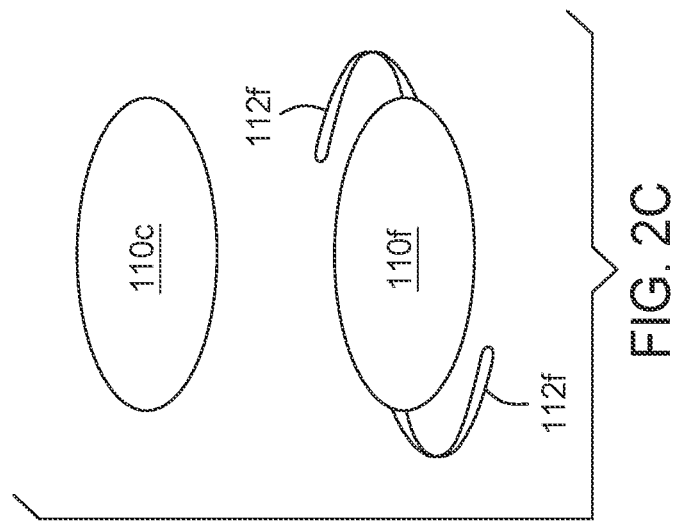
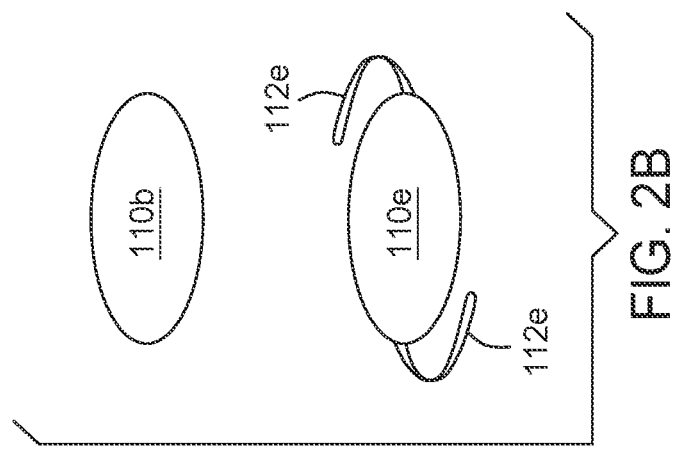
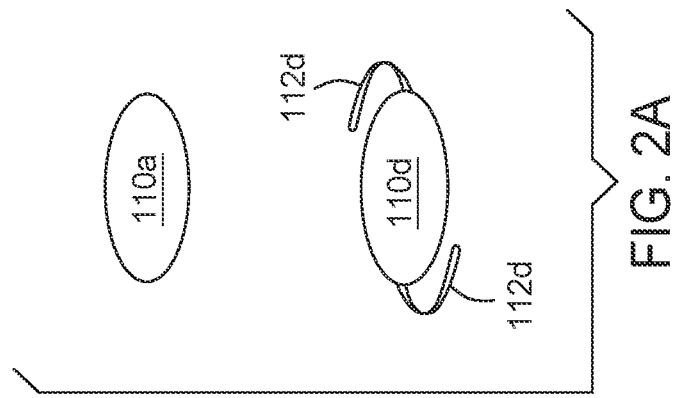

METHODS AND APPARATUS FOR PERFORMING OCULAR BIOMETRY

TECHNICAL FIELD

The present disclosure relates generally to methods and apparatus for performing ocular biometry.

BACKGROUND

An ophthalmic surgical procedure, referred to as combined phaco-vit, has gained in popularity across the globe. Combined phaco-vit involves performing both vitrectomy and phacoemulsification cataract surgery.

Vitrectomy is a type of eye surgery that treats problems with the retina or the vitreous. Vitrectomy may be performed as part of a vitreo-retinal procedure for treating conditions such as diabetic traction retinal detachment, diabetic vitreous hemorrhage, macular hole, retinal detachment, epimacular membrane, and many other ophthalmic conditions.

Phacoemulsification is a modern cataract surgery in which the eye's internal lens is emulsified with an ultrasonic handpiece and aspirated from the eye. An intraocular lens (IOL) is then implanted in the posterior lens capsule (hereinafter "the lens capsule") of the eye.

Combined phaco-vit procedures are performed, in certain cases, because the patient has a pre-existing cataract as well as a retinal condition that both need to be addressed. In certain other cases, combined phaco-vit procedures are performed because a patient with, for example, a retinal condition seeks help from a retinal surgeon, who identifies the retinal condition but also decides to perform cataract surgery based on the premise that the patient will, at some point in the future, need cataract surgery anyway. As a result, prior to performing the combined phaco-vit, the axial length of the patient's eye is typically measured in the doctor's office (i.e., not the operating room) using low coherence interferometry or ultrasound-based measurement techniques and devices. The curvature of the patient's cornea is also measured using a keratometer and other optical devices. Based on such measurements, an IOL with a certain refractive power is selected to be implanted in the eye. The selection of the IOL's refractive power and/or placement may be performed, based on the axial length and cornea curvature measurements, by a system using an IOL calculation algorithm.

However, ultrasound-based axial length measurements, which are less accurate than low coherence interferometry, are impossible or at least difficult to perform in the presence of certain types of retinal conditions, such a retinal detachment. Ultrasound-based axial length measurements can also be inaccurate in the presence of certain other types of retinal conditions, such as epimacular membranes, vitreomacular schisis, macular holes, or the vitreomacular traction syndrome. Similar to ultrasound-based measurements, performing axial length measurements with low coherence interferometry may also yield inaccurate results or be impossible in the presence of pre-operative vitreous hemorrhage, dense cataract, or retinal detachment. More specifically, for example, in the presence of pre-operative vitreous hemorrhage, low coherence interferometry, which is more accurate than ultrasonic measurements, may be impossible, which causes clinicians to use ultrasound techniques and devices that also provide inaccurate measurements in the presence of such conditions, as described above.

Therefore, often, an IOL that is selected based on axial length measurements of a patient's eye with retinal conditions, does not meet the expected refractive target. For example, the refractive power provided by such an IOL may be off by a few or many diopters from the refractive target. As such, after a surgeon performs the combined phaco-vit procedure and implants the IOL in the patient's eye, after surgery the patient experiences poor vision and is advised to wear glasses to compensate for the out of focus IOL.

BRIEF SUMMARY

The present disclosure relates generally to methods and apparatus for performing ocular biometry.

Certain embodiments provide a method of performing ocular biometry. The method includes performing phacoemulsification to emulsify and remove an internal lens of an eye. The method further includes performing vitrectomy to remove vitreous from the eye. The method also includes placing a trial in a lens capsule of the eye. The method further includes performing biometry with a first biometry system to provide measurements including at least one of an axial length of the eye, a curvature of a cornea of the eye, and toric axis. The method also includes removing the trial from the lens capsule.

Certain embodiments provide a biometry system including a memory comprising executable instructions and a processor in data communication with the memory and configured to execute the instructions to cause the biometry system to receive an indication to perform biometry on an eye, perform biometry on the eye, wherein the eye is aphakic, vitreous is removed from the eye, and a trial is placed in a lens capsule of the eye. The processor is further configured to cause the biometry system to provide a set of measurements based on the biometry.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

FIGS. 2A-2C illustrate example trials with different size, including trials with haptics as well as trials without haptics, in accordance with certain embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
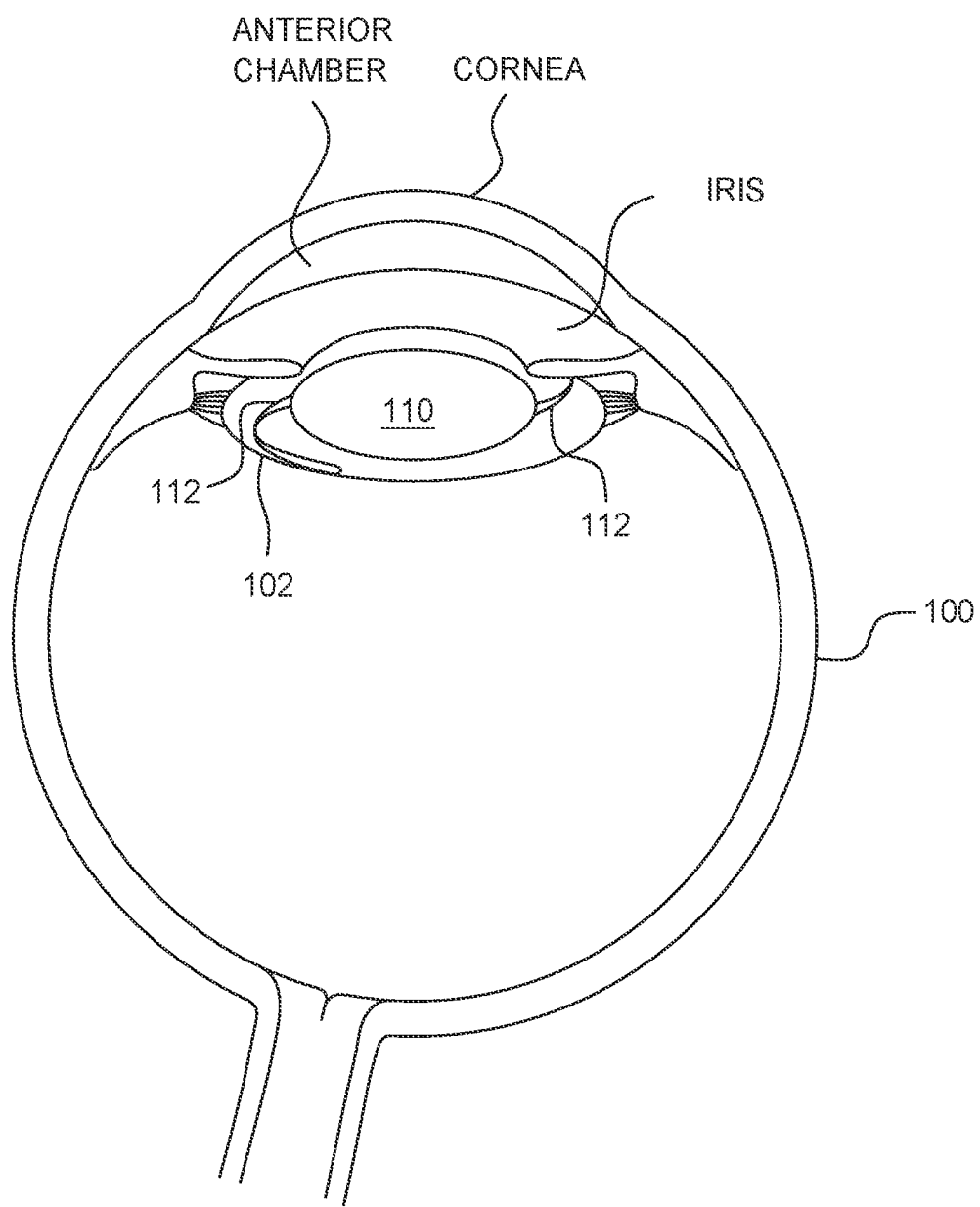
FIG. 1 illustrates an example of a trial that is placed inside of the lens capsule of an eye, in accordance with certain embodiments.

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

As described above, performing biometry, and especially, axial length measurements of an eye with retinal conditions often results in inaccurate measurements. Accordingly, certain embodiments described herein relate to intraoperative measurements of the axial length subsequent to addressing the eye's retinal conditions. More specifically, according to certain embodiments described herein, a surgeon may first perform phacoemulsification and next perform any necessary vitreo-retinal procedures to address retinal conditions that prevent optical measurements of the axial length of the eye. In certain cases, the surgeon may fill the eye with fluids (e.g., air, gas, perfluorocarbon fluid, silicone oil, etc.) as part of the vitreo-retinal procedure (e.g., to reattach the retina). Filling the eye with such substances after phacoemulsification may cause the lens capsule to distort in the fluid and lose its natural shape, including its curvature. The natural shape of the lens capsule refers to the shape of the lens capsule prior to phacoemulsification, when the natural lens is still in place. A biometry system, such as an optical coherence tomography system, however, may not be able to determine the shape and position of a loose or non-distended lens capsule. As determining the shape and position of a loose or non-distended lens capsule is an important aspect of providing accurate axial length measurements and/or measurement of the cornea curvature, a loose or non-distended lens capsule, therefore, negatively impacts the accuracy of the axial length measurements and/or other biometry measurements.

Accordingly, certain embodiments described herein provide a sterile device, also referred to as a trial or a temporary IOL, which may be placed in the lens capsule to hold the lens capsule in a known shape (e.g., a shape known to the biometry system as the shape of the lens capsule). In certain embodiment, the axial length measurement algorithm the biometry system is configured with may detect a lens capsule only when the lens capsule has a shape known to the algorithm as being the shape of a lens capsule. When the lens capsule conforms to a known shape, the effective lens position can be accurately determined by, for example, the biometry system. Accurately determining the effective lens position results in more accurate axial length measurements.

FIG. 1 illustrates an example of a trial 110 that is placed inside of the lens capsule 102 of an eye 100. Trial 110 includes haptics 112 that stabilize the position of trial 110 inside the lens capsule 102 as well as apply slight pressure to the inner surfaces of the lens capsule in order to cause the lens capsule to preserve its natural shape (e.g., re-conform to its known shape). In certain embodiments, trial 110 is foldable similar to a permanent IOL, as one of ordinary skill in the art appreciates. In certain embodiments, trial 110 includes material similar to the material used in a permanent IOL. In certain embodiments trial 110 includes material such as silicone hydrogel, acrylic, plastic, and other types of material generally used in permanent IOLs. Although in the example of FIG. 1 trial 110 includes haptics 112, in certain embodiments, trial 110 may be provided without haptics 112 and instead be sized and shaped similar to a natural lens to fill the entire or almost the entire space within the lens capsule 102. Example trials without haptics are shown as trials 110a, 110b, and 110c.

FIGS. 2A-2C illustrate three trials 110a-110c with different sizes but without haptics. FIGS. 2A-2C also illustrate three trials 110d-110f with different sizes, where each trial includes corresponding haptics 112. Trials 110 with different sizes may be provided to a surgeon in the operating room because different patients may have varying eye sizes and, therefore, varying lens capsule sizes. As such, for example, a surgeon may determine that to produce a known shape for the patient's lens capsule, a relatively large trial (e.g., trial 110c) may have to be used because of the relatively large size of the patient's lens capsule. In another example, the surgeon may determine that the patient's eye is relatively small and, therefore, a relatively smaller trial (e.g., trial 110a) may have to be used to ensure that the trial fits the lens capsule. Note that to produce a known shape for the lens capsule, it is not necessary for a surgeon to use a trial that exactly fits the size of the lens capsule. Further, note that trials 110d-110f are shown to illustrate that a surgeon may be provided with different sizes and types of trials. A surgeon may be provided with a larger or smaller selection of trials of different sizes and types. Also note that the sizes of trials 110 shown in FIGS. 2A-2C do not correspond to the sizes of actual trials that may be placed in a lens capsule.

In some embodiments, the different trials that are provided to the surgeon may all have the same curvature and/or refractive properties. In some other embodiments, each of the different trials may have a different curvature and/or refractive properties. When a surgeon selects a certain trial, the surgeon may indicate to a biometry system (e.g., a system that measures the axial length and the curvature of the cornea, etc.) what trial was selected and then place the trial in the lens capsule. In such embodiments, the biometry system is configured with information relating to the curvature of the selected trial 110 and/or its other properties, such as the refractive properties and optical powers etc. The biometry system is also configured with information relating to how the selected lens is supposed to perform optically in the presence of different types of fluids in the eye (e.g., air, gas, perfluorocarbon fluid, silicone oil, etc.). As such, the biometry system is able to utilize the information discussed above in its measurement of the axial length of the eye as well as other biometry measurements.

In certain embodiments, a trial may be an IOL whose properties (e.g., posterior curvature, refractive and optical power properties) are known to the biometry system. In such embodiments, the trial may be a certain IOL that is manufactured by an existing IOL manufacturer. The biometry system, in certain such embodiments, is configured with the properties of the IOL and the surgeons are advised to use that specific IOL for the biometry described herein. In certain embodiments, the biometry system may be configured with information relating to a number of different IOLs manufactured by different manufacturers. In such embodiments, the surgeon may select the IOL, that is going to be temporarily used for the biometry described herein, on a user interface of the biometry system. The biometry system the provides measurements based on the properties of the selected IOL.

FIGS. 3-8 illustrate flow diagrams corresponding to operations performed to provide accurate biometry measurements of a patient's eye, wherein each of FIGS. 3-8 illustrates different operations depending on several factors, such as the retinal condition of the eye. Based on the accurate biometry measurements, in each of FIGS. 3-8 an IOL may be selected to achieve a desired refractive target. Note that FIGS. 3-8 illustrate surgical procedures that may be performed manually by a surgeon, performed by a surgeon using a master-slave robotic system, or performed using an image-guided robotic system (e.g., OCT guided robotic system). For example, phacoemulsification, vitreo-retinal procedures, or other procedures discussed in FIGS. 3-8 may be performed in one of the ways discussed above.

Figure 3:
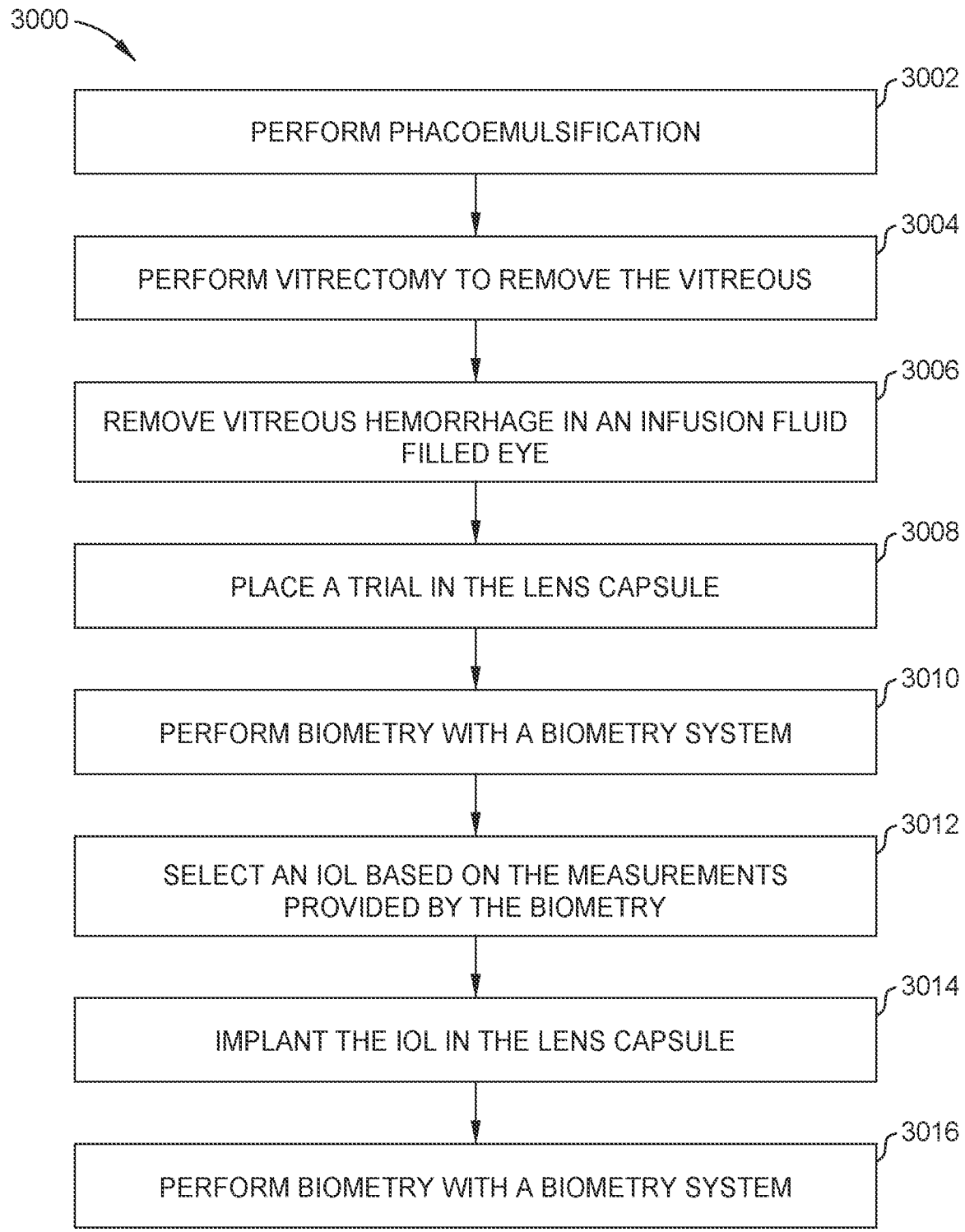
FIG. 3 illustrates example operations performed on a patient's eye with vitreous hemorrhage to provide accurate biometry measurements for the eye, in accordance with certain embodiments.

FIG. 3 illustrates example operations 3000 performed on a patient's eye with vitreous hemorrhage to provide accurate biometry measurements for the eye, in accordance with certain embodiments.

At step 3002, phacoemulsification is performed.

At step 3004, vitrectomy is performed to remove the vitreous.

At step 3006, vitreous hemorrhage is removed in an infusion fluid (e.g., balanced salt solution (BSS)) filled eye.

At step 3008, a temporary trial is placed in the lens capsule. In certain embodiments, multiple trials with different sizes may be available for selection, as shown in FIGS. 2A-2C. In certain such embodiments, one of the trials that is more likely to match the size of the patient's lens capsule may be selected and placed in the lens capsule.

At step 3010, biometry is performed on the patient's eye using intraoperative OCT (hereinafter "iOCT"), swept source biometry, and/or intraoperative aberrometry to determine the axial length of the eye, the toric axis and/or an angle thereof (for correcting astigmatism), the curvature of the cornea, and/or any other relevant measurements. In certain embodiments, each one of iOCT, swept source biometry, and intraoperative aberrometry may be performed by a different biometry system. In certain other embodiments, a single biometry system may perform two or more of iOCT, swept source biometry, and intraoperative aberrometry.

Note that the biometry system takes into account the refractive index of the infusion fluid (e.g., BSS) that fills the eye, when calculating one or more of the measurements described above. For example, in certain embodiments, the biometry system is configured to receive an indication relating to the substance that fills the eye. The biometry system then selects the refractive index, from a list of refractive indices that corresponds to the substance indicated by the surgical indication. In certain embodiments, the indication may be received through a user interface of the biometry system. For example, in certain embodiments of FIG. 3, a user (e.g., surgeon) may select BSS on the user interface of the biometry system. As a result, any biometry calculations then are based on the refractive index of BSS.

In certain embodiments where the surgeon has access to different trials with different curvatures and refractive indices, after selecting one of the trials, the surgeon may indicate, to the biometry system (e.g., through a user interface of the biometry system), the trial that has been selected and placed in the lens capsule. In certain such embodiments, the biometry system may be configured to base certain biometry measurements on the properties (e.g., curvature, refractive index, etc.) of the selected trial.

At step 3012, an IOL is selected based on the measurements provided by the biometry performed at step 3010. For example, an IOL selection algorithm may be used (e.g., by the biometry system or some other system) to select an IOL that meets a certain refractive target based on the measurements provided by the biometry performed at step 3010.

At step 3014, the IOL selected at step 3012 is implanted in the lens capsule. For example, after biometry is performed at step 3010, the trial may be taken out of the lens capsule and the selected IOL may be implanted instead.

At step 3016, biometry may be performed on the patient's eye again with the IOL implanted in the lens capsule. In certain embodiments, the biometry may be performed using iOCT, swept source OCT, and/or intraoperative aberrometry. The biometry at step 3016 is performed while the former vitreous cavity is filled with air, gas, perfluorocarbon fluid, or silicone oil, or an alternative vitreous substitute with known refractive index. Further, the biometry at step 3016 is performed in order to determine if the correct IOL was implanted. For example, if the biometry that is performed at step 3016 indicates that the implanted IOL does not meet the refractive target, a different IOL may be used. In certain embodiments, the biometry system or method used at step 3016 may be the same as the biometry system or method used at step 3010 or a different biometry system or method.

Figure 4:
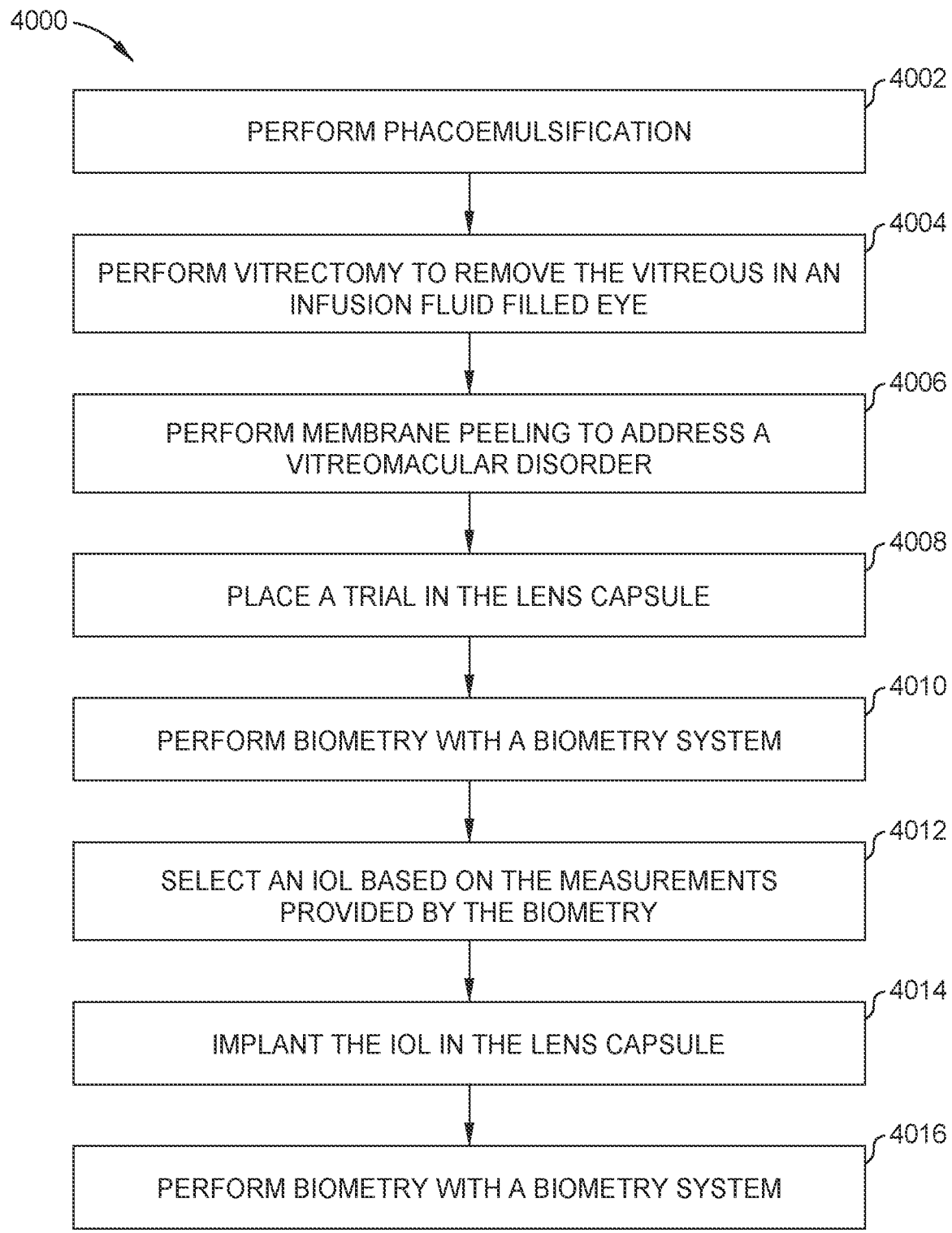
FIG. 4 illustrates operations performed on a patient's eye with a vitreomacular disorder to provide accurate biometry measurements for the eye, in accordance with certain embodiments.

FIG. 4 illustrates example operations 4000 performed on a patient's eye with a vitreomacular disorder to provide accurate biometry measurements for the eye, in accordance with certain embodiments.

At step 4002, phacoemulsification is performed.

At step 4004, vitrectomy is performed to remove the vitreous in an infused fluid filled eye.

At step 4006, membrane peeling is performed to address the vitreomacular disorder. For example, the internal limiting membrane (ILM), epiretinal membrane, or other types of membrane, may be peeled at the macula during vitrectomy. As a result of the peeling, macular elevation may be reduced, therefore, allowing optical systems and techniques to be used for correctly measuring the axial length of the eye.

At step 4008, a temporary trial is placed in the lens capsule. In certain embodiments, multiple trials with different sizes may be available for selection, as shown in FIGS. 2A-2C. In certain such embodiments, one of the trials that is more likely to match the size of the patient's lens capsule may be selected and placed in the lens capsule.

At step 4010, biometry is performed on the patient's eye using iOCT, swept source biometry, and/or intraoperative aberrometry to determine the axial length of the eye, the toric axis and/or an angle thereof (for correcting astigmatism), the curvature of the cornea, and/or any other relevant measurements. In certain embodiments, each one of iOCT, swept source biometry, and intraoperative aberrometry may be performed by a different biometry system. In certain other embodiments, a single biometry system may perform two or more of iOCT, swept source biometry, and intraoperative aberrometry.

Note that, as discussed, in certain embodiments, the biometry system takes into account the refractive index of the infusion fluid (e.g., BSS) that fills the former vitreous cavity, when calculating one or more of the measurements described above.

In certain embodiments where the surgeon has access to different trials with different curvatures and refractive indices, after selecting one of the trials, the surgeon may indicate, to the biometry system (e.g., through a user interface of the biometry system), the trial that has been selected and placed in the lens capsule. In certain such embodiments, the biometry system may be configured to base certain biometry measurements on the properties (e.g., curvature, refractive index, etc.) of the selected trial.

At step 4012, an IOL is selected based on the measurements provided by the biometry performed at step 4010. For example, an IOL selection algorithm may be used to select an IOL that meets a certain refractive target based on the measurements provided by the biometry performed at step 4010.

At step 4014, the IOL selected at step 4012 is implanted in the capsule. For example, after biometry is performed at step 4010, the trial may be taken out of the lens capsule and the selected IOL may be implanted instead.

At step 4016, biometry may be performed on the patient's eye again with the IOL implanted in the lens capsule. In certain embodiments, the biometry may be performed using iOCT, swept source, and/or intraoperative aberrometry. The biometry at step 4016 is performed while the former vitreous cavity is filled with air, gas, perfluorocarbon fluid, or silicone oil, or an alternative vitreous substitute. Further, the biometry at step 4016 is performed in order to determine if the correct IOL was implanted. For example, if the biometry that is performed at step 4016 indicates that the implanted IOL does not meet the refractive target, a different IOL may be used. In certain embodiments, the biometry system or method used at step 4016 may be the same as the biometry system or method used at step 4010 or a different biometry system or method.

Figure 5:
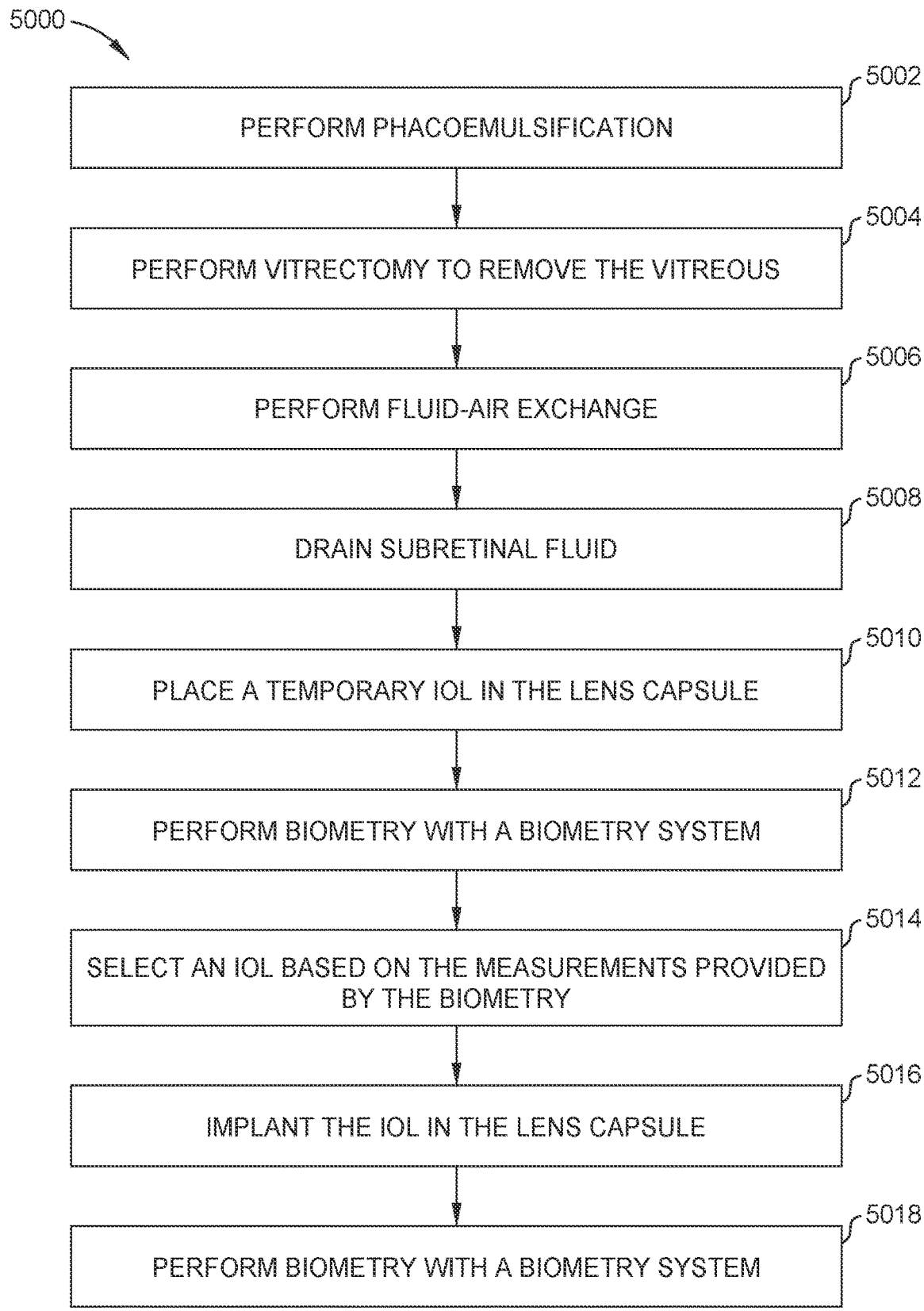
FIG. 5 illustrates example operations performed on a patient's eye with a detached retina to provide accurate biometry measurements for the eye, in accordance with certain embodiments.

FIG. 5 illustrates example operations 5000 performed on a patient's eye with a detached retina to provide accurate biometry measurements for the eye, in accordance with certain embodiments.

At step 5002, phacoemulsification is performed.

At step 5004, vitrectomy is performed to remove the vitreous as infusion fluid fills the eye.

At step 5006, fluid-air exchange is performed to replace the fluid, which is infused in the eye (e.g., balanced salt solution (BSS)) during removal of the vitreous, with air. As described above, air may be used to reattach the retina. In certain embodiments, instead of air, a different type of gas may be used to reattach the retina.

At step 5008, the sub-retinal fluid is drained. Steps 5006 and 5008 are performed to intraoperatively reattach the retina. Additional steps, such as photocoagulation may be performed to permanently attach the retina but such steps are not described here for brevity. As discussed, intraoperatively attaching the retina allows for the use of optical techniques and devices for performing biometry.

At step 5010, a temporary trial is placed in the lens capsule. In certain embodiments, multiple trials with different sizes may be available for selection, as shown in FIGS. 2A-2C. In certain such embodiments, one of the trials that is more likely to match the size of the patient's lens capsule may be selected and placed in the lens capsule.

At step 5012, biometry is performed on the patient's eye using intraoperative OCT iOCT, swept source biometry, and/or intraoperative aberrometry to determine the axial length of the eye, the toric axis and/or an angle thereof (for correcting astigmatism), the curvature of the cornea, and/or any other relevant measurements. In certain embodiments, each one of iOCT, swept source biometry, and intraoperative aberrometry may be performed by a different biometry system. In certain other embodiments, a single biometry system may perform two or more of iOCT, swept source biometry, and intraoperative aberrometry. Note that, in certain embodiments, the biometry system takes into account the refractive index of air (or whatever gas or mixture of gases are used to fill the former vitreous cavity) when calculating one or more of the measurements described above. For example, in certain embodiments of FIG. 5, a user (e.g., surgeon) may select "air" on the user interface of the biometry system. As a result, any biometry calculations are then based on the refractive index of air.

In certain embodiments where the surgeon has access to different trials with different curvatures and refractive indices, after selecting one of the trials, the surgeon may indicate, to the biometry system (e.g., through a user interface of the biometry system), the trial that has been selected and placed in the lens capsule. In certain such embodiments, the biometry system may be configured to base certain biometry measurements on the properties (e.g., curvature, refractive index, etc.) of the selected trial.

At step 5014, an IOL is selected based on the measurements provided by the biometry performed at step 5010. For example, an IOL selection algorithm may be used to select an IOL that meets a certain refractive target based on the measurements provided by the biometry performed at step 5010.

At step 5016, the IOL selected at step 5014 is implanted in the capsule. For example, after biometry is performed at step 5010, the trial may be taken out of the lens capsule and the selected IOL may be implanted instead.

At step 5018, biometry may be performed on the patient's eye again with the IOL implanted in the lens capsule. In certain embodiments, the biometry may be performed using iOCT, swept source OCT, and/or intraoperative aberrometry. The biometry at step 5018 is performed while the former vitreous cavity is filled with air, gas, perfluorocarbon fluid, or silicone oil, or an alternative vitreous substitute. Further, the biometry at step 5018 is performed in order to determine if the correct IOL was implanted. For example, if the biometry that is performed at step 5018 indicates that the implanted IOL does not meet the refractive target, a different IOL may be used. In certain embodiments, the biometry system or method used at step 5018 may be the same as the biometry system or method used at step 5012 or a different biometry system or method.

Figure 6:
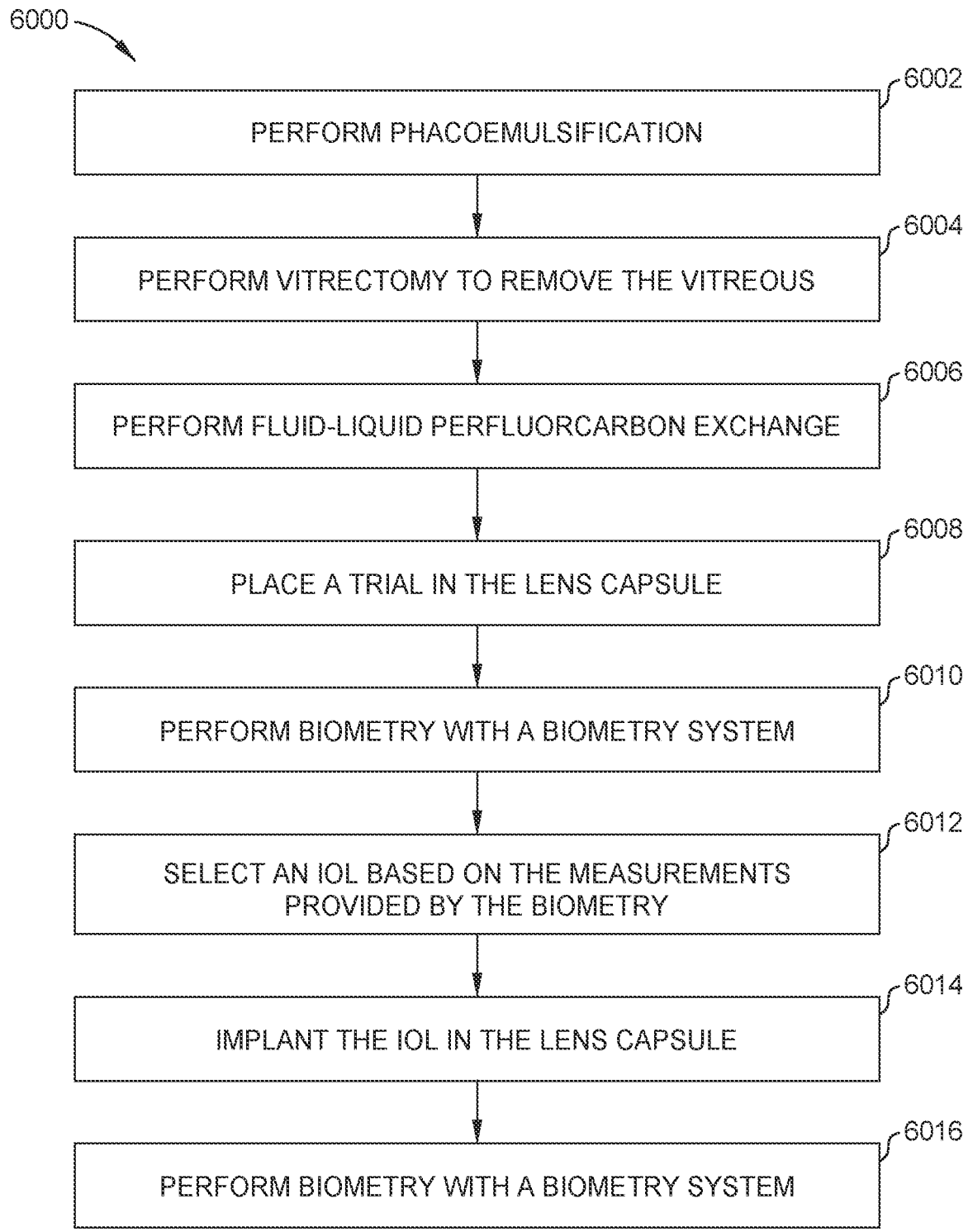
FIG. 6 illustrates example operations performed on patient's eye with a detached retina to provide accurate biometry measurements for the eye, in accordance with certain embodiments.

FIG. 6 illustrates example operations 6000 performed on patient's eye with a detached retina, in accordance with certain embodiments.

At step 6002, phacoemulsification is performed.

At step 6004, vitrectomy is performed to remove the vitreous in an infused fluid filled eye to provide accurate biometry measurements for the eye, in accordance with certain embodiments.

At step 6006, fluid-liquid perfluorocarbon exchange is performed to replace the fluid that is infused in the eye during removal of the vitreous with liquid perfluorocarbon. As described above, liquid perfluorocarbon may be used to reattach the retina. Additional steps, such as photocoagulation may be performed to permanently attach the retina but such steps are not described here for brevity.

At step 6008, a temporary trial is placed in the lens capsule. In certain embodiments, multiple trials with different sizes may be available for selection, as shown in FIGS.

2A-2C. In certain such embodiments, one of the trials that is more likely to match the size of the patient's lens capsule may be selected and placed in the lens capsule.

At step 6010, biometry is performed on the patient's eye using intraoperative OCT iOCT, swept source biometry, and/or intraoperative aberrometry to determine the axial length of the eye, the toric axis and/or an angle thereof (for correcting astigmatism), the curvature of the cornea, and/or any other relevant measurements. In certain embodiments, each one of iOCT, swept source biometry, and intraoperative aberrometry may be performed by a different biometry system. In certain other embodiments, a single biometry system may perform two or more of iOCT, swept source biometry, and intraoperative aberrometry. Note that the biometry system takes into account the refractive index of liquid perfluorocarbon when calculating one or more of the measurements described above. For example, in certain embodiments of FIG. 6, a user (e.g., surgeon) may select "liquid perfluorocarbon" on the user interface of the biometry system. As a result, any biometry calculations are then based on the refractive index of liquid perfluorocarbon.

In certain embodiments where the surgeon has access to different trials with different curvatures and refractive indices, after selecting one of the trials, the surgeon may indicate, to the biometry system (e.g., through a user interface of the biometry system), the trial that has been selected and placed in the lens capsule. In certain such embodiments, the biometry system may be configured to base certain biometry measurements on the properties (e.g., curvature, refractive index, etc.) of the selected trial.

At step 6012, an IOL is selected based on the measurements provided by the biometry performed at step 6010. For example, an IOL selection algorithm may be used to select an IOL that meets a certain refractive target based on the measurements provided by the biometry performed at step 6010.

At step 6014, the IOL selected at step 6012 is implanted in the capsule. For example, after biometry is performed at step 6010, the trial may be taken out of the lens capsule and the selected IOL may be implanted instead.

At step 6016, biometry may be performed on the patient's eye again with the IOL implanted in the lens capsule. In certain embodiments, the biometry may be performed using iOCT, swept source, and/or intraoperative aberrometry. The biometry at step 6016 is performed while the former vitreous cavity is filled with air, gas, perfluorocarbon fluid, or silicone oil, etc. Further, the biometry at step 6016 is performed in order to determine if the correct IOL was implanted. For example, if the biometry that is performed at step 6016 indicates that the implanted IOL does not meet the refractive target, a different IOL may be used. In certain embodiments, the biometry system or method used at step 6016 may be the same as the biometry system or method used at step 6010 or a different biometry system or method.

Figure 7:
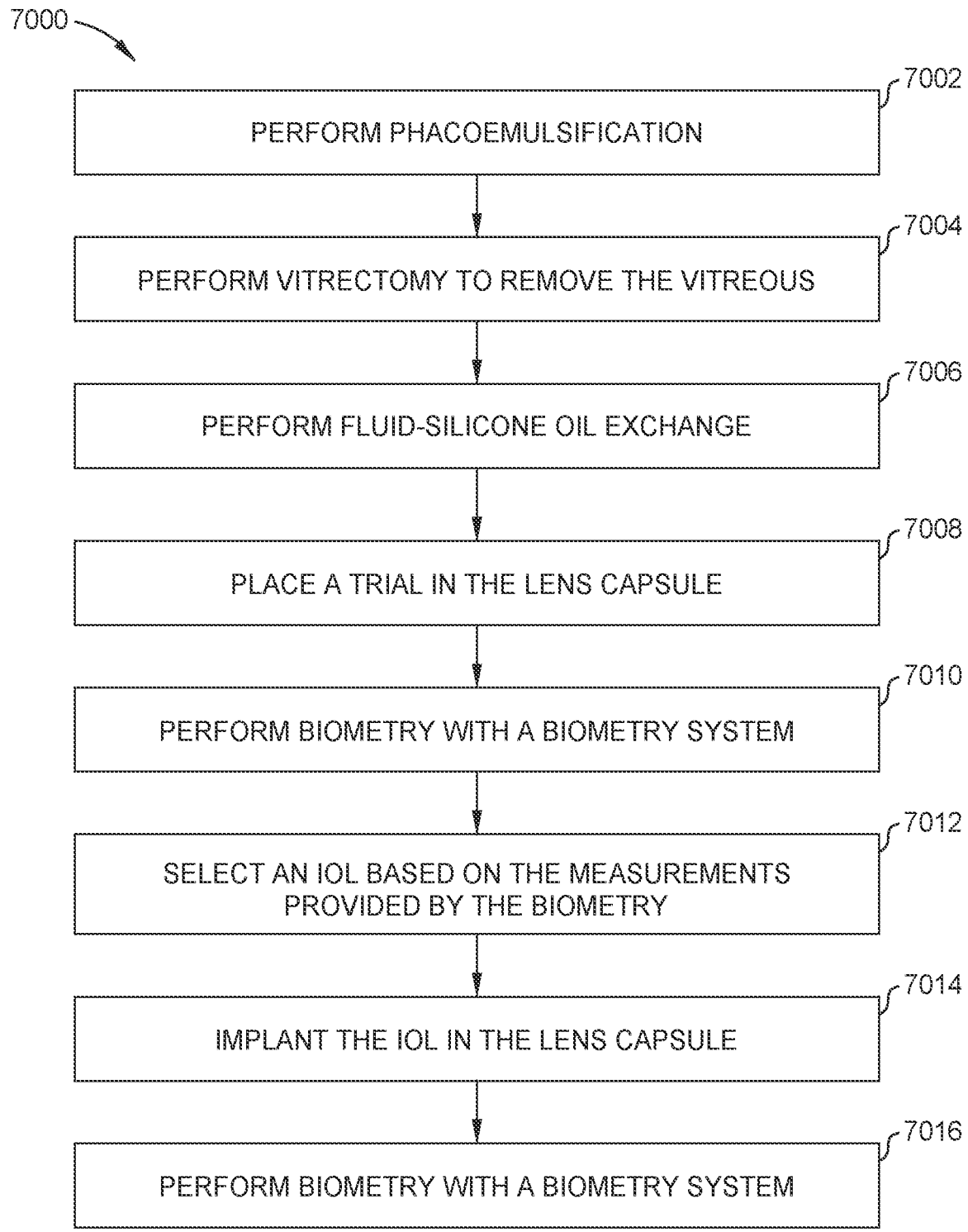
FIG. 7 illustrates example operations performed on a patient's eye with a detached retina to provide accurate biometry measurements for the eye, in accordance with certain embodiments.

FIG. 7 illustrates example operations 7000 performed on a patient's eye with a detached retina to provide accurate biometry measurements for the eye, in accordance with certain embodiments.

At step 7002, phacoemulsification is performed.

At step 7004, vitrectomy is performed to remove the vitreous in an infused fluid filled eye.

At step 7006, fluid-silicone oil exchange is performed to replace the fluid that is infused in the eye during removal of the vitreous with silicone oil. As described above, silicone oil may be used to reattach the retina. In certain embodiments, additional steps, such as photocoagulation may be performed to permanently attach the retina but such steps are not described here for brevity.

At step 7008, a temporary trial is placed in the lens capsule. In certain embodiments, multiple trials with different sizes may be available for selection, as shown in FIGS. 2A-2C. In certain such embodiments, one of the trials that is more likely to match the size of the patient's lens capsule may be selected and placed in the lens capsule.

At step 7010, biometry is performed on the patient's eye using intraoperative OCT iOCT, swept source biometry, and/or intraoperative aberrometry to determine the axial length of the eye, the toric axis and/or an angle thereof (for correcting astigmatism), the curvature of the cornea, and/or any other relevant measurements. In certain embodiments, each one of iOCT, swept source biometry, and intraoperative aberrometry may be performed by a different biometry system. In certain other embodiments, a single biometry system may perform two or more of iOCT, swept source biometry, and intraoperative aberrometry. Note that the biometry system takes into account the refractive index of silicone oil when calculating one or more of the measurements described above. For example, in certain embodiments of FIG. 7, a user (e.g., surgeon) may select "silicone oil" on the user interface of the biometry system. As a result, any biometry calculations are then based on the refractive index of silicone oil.

In certain embodiments where the surgeon has access to different trials with different curvatures and refractive indices, after selecting one of the trials, the surgeon may indicate, to the biometry system (e.g., through a user interface of the biometry system), the trial that has been selected and placed in the lens capsule. In certain such embodiments, the biometry system may be configured to base certain biometry measurements on the properties (e.g., curvature, refractive index, etc.) of the selected trial.

At step 7012, an IOL is selected based on the measurements provided by the biometry performed at step 7010. For example, an IOL selection algorithm may be used to select an IOL that meets a certain refractive target based on the measurements provided by the biometry performed at step 7010.

At step 7014, the IOL selected at step 7012 is implanted in the capsule. For example, after biometry is performed at step 7010, the trial may be taken out of the lens capsule and the selected IOL may be implanted instead.

At step 7016, biometry may be performed on the patient's eye again with the IOL implanted in the lens capsule. In certain embodiments, the biometry may be performed using iOCT, swept source biometry, and/or intraoperative aberrometry. The biometry at step 7016 is performed while the former vitreous cavity is filled with air, gas, perfluorocarbon fluid, or silicone oil, or an alternative vitreous substitute. Further, the biometry at step 7016 is performed in order to determine if the correct IOL was implanted. For example, if the biometry that is performed at step 7016 indicates that the implanted IOL does not meet the refractive target, a different IOL may be used. In certain embodiments, the biometry system or method used at step 7010 may be the same as the biometry system or method used at step 7016 or a different biometry system or method.

Figure 8:
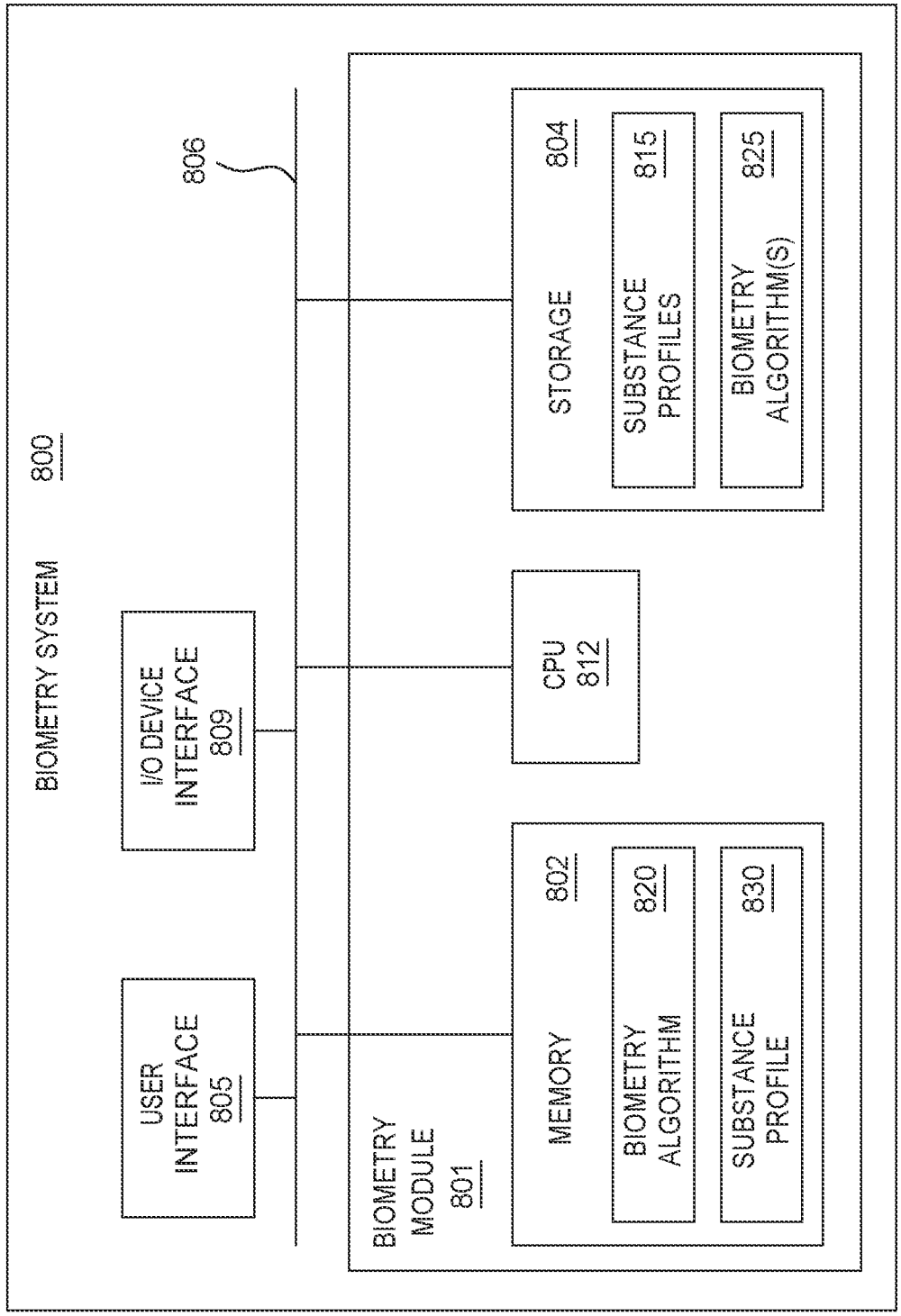
FIG. 8 illustrates an exemplary diagram showing how various components of an example biometry system communicate and operate together, in accordance with certain embodiments.

FIG. 8 illustrates an exemplary diagram showing how various components of an example biometry system 800 communicate and operate together. Biometry system 800 may be configured to perform iOCT, swept source biometry, and/or intraoperative aberrometry. Details regarding the various components biometry system 800 may include to perform iOCT, swept source biometry, and/or intraoperative aberrometry are known to one of ordinary skill in the art and are, therefore, omitted for brevity. In addition, details relating to how OCT, swept source biometry, and intraoperative aberrometry are performed are similarly omitted. Note that, as one of ordinary skill in the art appreciates, in certain embodiments, biometry system 800 includes or is in communication with an OCT scanner (not shown) that is configured as a time domain OCT (TD-OCT). In certain embodiments, biometry system 800 includes or is in communication with an OCT scanner that is configured as a frequency domain OCT (FD-OCT). In certain embodiments, biometry system 800 includes or is in communication with an OCT scanner that is configured as a swept-source OCT (SS-OCT). In certain embodiments, biometry system 800 includes or is in communication with an OCT scanner that is configured as a spectral domain-based OCT. In certain embodiments, biometry system 800 includes or is in communication with an OCT scanner that is configured to provide OCT biometry (e.g., B-OCT). In some implementations, the scan data generated by the OCT scanner may include two-dimensional (2D) scan data of a line scan (B-scan). The scan information provided by an OCT scanner of any of the types described above may be used for performing axial length measurements, as described herein.

As shown, biometry system 800 includes, without limitation, biometry module 801, user interface display 805, an interconnect 806, and at least one I/O device interface 809, which may allow for the connection of various I/O devices (e.g., keyboards, displays, mouse devices, pen input, etc.) to biometry system 800.

Biometry module 801 includes a processor or central processing unit (CPU) 812, a memory 802, and storage 804. CPU 812 may retrieve and execute programming instructions stored in the memory 802. Similarly, CPU 812 may retrieve and store application data residing in memory 802. Interconnect 806 transmits programming instructions and application data, among CPU 812, I/O device interface 809, user interface display 805, memory 802, storage 804, etc. CPU 812 can represent a single CPU, multiple CPUs, a single CPU having multiple processing cores, and the like. Additionally, in certain embodiments, memory 802 represents volatile memory (e.g., random access memory). Furthermore, in certain embodiments, storage 804 represents non-volatile memory (e.g., a disk drive). Although shown as a single unit, storage 804 may be a combination of fixed or removable storage devices, such as fixed disc drives, removable memory cards or optical storage, network attached storage (NAS), or a storage area-network (SAN).

Memory 802 includes instructions, which when executed by the processor, performs an operation for performing biometry, as described in the embodiments herein. For example, according to embodiments described herein, storage 804 stores profiles 815 of various substances (e.g., air, gas, liquid perfluorocarbon, silicone oil, etc.). The profile of each of these substances indicates information about the substance, such as the refractive index of the substance. Storage 804 may also store trial profiles (not shown), where each trial profile indicates information (e.g., curvature, refractive index, etc.) about the trial that is selected and placed in the lens capsule for the purpose of performing biometry. Storage 804 may also store various biometry algorithms 825 for measuring the axial length of the eye, the toric axis and/or an angle thereof (for correcting astigmatism), the curvature of the cornea, as well as any other relevant measurements. For example, biometry algorithms 825 may include algorithms that configure biometry system 800 to perform iOCT, swept source OCT, and/or intraoperative aberrometry. As described above, in certain embodiments, biometry system 800 be configured to perform at least one of iOCT, swept source OCT, and/or intraoperative aberrometry.

In operation, a medical professional may select through user interface 805 the type of biometry that needs to be performed. In response, CPU 812 retrieves the corresponding biometry algorithm 830 from storage 804 from biometry algorithm(s) 825 and then causes biometry algorithm 830 to be stored in memory 802. The medical professional may also select the type of substance that fills the former vitreous cavity, in response to which CPU 812 retrieves the corresponding substance profile 830 for storage in memory 802. In addition, the medical professional may indicate which trial the surgeon has placed in the eye, in response to which CPU 812 retrieves the corresponding trial profile from storage 804 and then causes the trial profile to be stored in memory 802. CPU 812 then executes biometry algorithm 820, which may use substance profile 830 and/or the trial profile to provide a set of measurements.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

EXAMPLE EMBODIMENTS

Embodiment 1: A biometry system, comprising: a memory comprising executable instructions; a processor in data communication with the memory and configured to execute the instructions to cause the biometry system to: receive an indication to perform biometry on an eye; perform biometry on the eye, wherein: the eye is aphakic; vitreous is removed from the eye; a trial is placed in a lens capsule of the eye; provide a set of measurements based on the biometry. The retina is re-attached prior to the biometry.

What is claimed is:

1. A method of performing ocular biometry during a combined phacoemulsification and vitrectomy procedure, comprising:
    performing phacoemulsification to emulsify and remove an internal lens of an eye;
    performing vitrectomy to remove vitreous from the eye;
    placing a trial in a lens capsule of the eye;
    after performing the vitrectomy to remove vitreous from the eye and while the trial is in the lens capsule of the eye, performing biometry with a first biometry system to provide measurements including at least one of an axial length of the eye, a curvature of a cornea of the eye, and toric axis; and
    removing the trial from the lens capsule.

2. The method of claim 1, further comprising: selecting an intraocular lens (IOL) based on the measurements; and implanting the IOL in the lens capsule after the trial is removed.

3. The method of claim 2, further comprising: performing biometry with the biometry system or another biometry system, subsequent to implanting the IOL.

4. The method of claim 1, further comprising: removing vitreous hemorrhage prior to placing the trial in the lens capsule.

5. The method of claim 1, further comprising: performing membrane peeling to address a vitreomacular disorder prior to placing the trial in the lens capsule.

6. The method of claim 1, further comprising: performing fluid-air exchange to replace fluids in the eye with air; and draining a sub-retinal fluid prior to placing the trial in the lens capsule.

7. The method of claim 1, further comprising: performing fluid-liquid perfluorocarbon exchange to replace fluids in the eye with liquid perfluorocarbon prior to placing the trial in the lens capsule.

8. The method of claim 1, further comprising: performing fluid-silicone oil exchange to replace fluids in the eye with silicone oil prior to placing the trial in the lens capsule.

9. The method of claim 1, wherein the first biometry system is configured to perform at least one of an intraoperative optical coherence tomography (iOCT), swept source biometry, and intraoperative aberrometry.

10. The method of claim 1, wherein the measurements are based on at least one of: a refractive index of a substance that fills the eye when the first biometry system performs the biometry, a curvature of the trial, and a refractive index of the trial.

* * * * *